United States Patent [19]

Schajer

[11] Patent Number: 4,941,357

[45] Date of Patent: Jul. 17, 1990

[54] METHOD FOR ESTIMATING THE STRENGTH OF WOOD

[75] Inventor: Gary S. Schajer, Federal Way, Wash.

[73] Assignee: Weyerhaeuser Company, Tacoma, Wash.

[21] Appl. No.: 288,534

[22] Filed: Dec. 23, 1988

[51] Int. Cl.⁵ ............................................. G01M 3/24
[52] U.S. Cl. ...................................................... 73/600
[58] Field of Search ................... 73/866, 87, 573, 580, 73/582, 600, 598, 32 A; 250/358.1, 359.1

[56] References Cited

U.S. PATENT DOCUMENTS 4,350,044 9/1982 Richardson et al. .................. 73/600
4,817,021 3/1989 Sowerby et al. ............ 250/359.1 X Primary Examiner—Jerry W. Myracle

[57] ABSTRACT

This invention provides an improved method for estimating the strength or stiffness of a piece of wood by measuring the longitudinal density profile of the wood. The density profile of the wood is determined by measuring the absorption or other modification of radiation at a sequence of local areas in the wood. The strength or stiffness estimation method identifies and quantifies those features in the wood density profile which describe two of the main wood factors that control overall wood strength or stiffness, i.e. the inherent (clear) wood strength or stiffness and the wood structural effect. The inherent wood strength or stiffness is mainly identified by the areas relatively constant density between knots, and the wood structural effect is mainly identified by the sharp density increases caused by knots. The strength or stiffness estimate for the wood combines these two factors.

11 Claims, 2 Drawing Sheets

METHOD FOR ESTIMATING THE STRENGTH OF WOOD

BACKGROUND OF THE INVENTION

Efficient utilization of lumber production requires that the material be graded according to its intended use. In this way an effective and economic match can be made between the lumber needs of end-users and the lumber supply of the producer. Many factors control the suitability of lumber for any particular purpose. They include the degree of straightness, the amount of any wane, and the presence and size of knots, splits, shakes, etc. These and other factors are currently assessed by trained personnel using established visual grade rules.

Two engineering properties are often of great importance when designing wood structures. They are wood strength and wood stiffness. In the visual system of grading, these properties are established from values measured during destructive tests on extensive samples of each visual grade. However, the process of visual grading is not very effective at identifying wood strength and stiffness. Thus, a sample of material of a given visual grade contains pieces whose strengths and stiffnesses vary over very wide ranges. For example, the strength of the strongest piece in a batch of a given visual grade is typically 5-10 times that of the weakest piece. Thus, for safe design, the strength and stiffness of the worst likely piece has to be assumed. This is clearly very wasteful of the majority of superior pieces which are being used at well below their actual capacities.

Such waste can be reduced by developing and using techniques which better identify the superior pieces and reliably distinguish them from the inferior pieces. This process is called "Machine Stress Rating" or "MSR". A method which has been developed for this purpose involves measuring lumber stiffness in the plank bending mode. For example, a machine which is commonly used for this purpose is the "Continuous Lumber Tester", made by Metriguard Inc., of Pullman, Wash. This machine measures plank stiffness by moving the wood longitudinally through a series of instrumented rollers. These rollers are slightly displaced from a straight line so as to bend the wood by predetermined amounts, first in one direction and then in the other. The machine then infers the wood plank stiffness from the bending forces measured by the instrumented rollers.

Plank bending stiffness is an excellent indicator of the stiffness in the joist bending mode, which is the most common design configuration. The plank stiffness is also a modest indicator of tensile and bending strength. Using measured statistical relationships between plank stiffness and strength, and also visual over-rides for knots and other defects, lumber is segregated into various strength grades.

The machine stress rating process based on plank stiffness measurements is an improvement over visual grading as an indicator of wood strength. However, it is far from ideal because the range of strengths in each MSR grade remains quite large. Thus, most pieces must still be used at well below their capacity. Additional wastage of material strength capacity occurs because the imprecise grading method often incorrectly assigns strong material to low strength grades.

Another difficulty with wood strength grading by plank stiffness measurement is that typical machines for measuring stiffness are physically large, mechanically complex, and costly to maintain. Also, they are insensitive to the stiffness of the material close to the ends of the lumber. Thus, several feet of each board remain ungraded.

This invention describes a more precise and reliable method of wood strength grading based on measurements of wood density (specific gravity) profile. It achieves a superior level of precision by more accurately identifying the features which control wood strength. The procedure also greatly enhances the engineering performance of the lumber when it is specified according to a reliability based design format. An additional advantage of this invention over the plank stiffness method is that the hardware is compact and easy to maintain. It makes non-contacting measurements over the entire length of the wood, right up to the two ends. The density profile method can also make modestly precise estimates of lumber stiffness, of similar statistical precision to the strength estimates available from measurements of plank stiffness. These stiffness estimates are inferior to those available by direct stiffness measurement, and form only a subsidiary objective of this invention.

SUMMARY OF THE INVENTION

The present invention is an improved method and apparatus for strength grading of wood in most stages of breakdown from log form to finished dimension lumber. It involves measurement of the density (specific gravity) profile of the wood along its length. Strength predictions are made by identifying and quantifying two of the main wood factors that control overall wood strength. They are:

1. inherent (clear) wood strength
2. wood structural effect

The inherent (clear) wood strength depends on the material characteristics of the wood substance itself. The wood structural effect is a strength reducing effect which depends on the geometric arrangement of the wood substance as influenced by such things as the presence of knots and the resulting local grain distortions.

These two strength controlling factors are identified and quantified through measurements of wood density profile. Wood density in a localized area can be measured in a number of ways. A convenient way uses gamma rays, X-rays or other forms of radiation. The radiation is absorbed within the wood according to the local density. By measuring the amount of radiation absorption, the local density can be determined.

When local density is measured at many points along the length, and commonly also across the width of the wood, sharp localized increases in wood density are observed. These density increases typically correspond to the presence of knots. The larger the knot or knot combination, in general the larger is the associated density increase. The measured density increases occur because the density of the material in a knot is typically about twice that of the adjacent clear wood.

Measurements of wood density profiles allow identification and quantification of the two strength controlling factors described above. The density of the clear wood between knots indicates the inherent wood strength. Higher density indicates higher inherent wood strength. The size of localized density increases are good descriptors of the structural effect. This is because the measured localized density increases indicate the presence and size of knots. These knots form a major part of the wood structural effect. Larger localized density increases correspond to larger knots, which in turn correspond to a larger strength reducing structural effect. This invention makes measurements of the two strength controlling factors, and combines them to form a reliable estimate of the overall wood strength.

This invention solves many of the problems inherent in the plank stiffness measurement method of estimating wood strength. For example, the stiffness method uses the minimum measured stiffness along the length of a piece of lumber, together with visually observed knot sizes and locations, to indicate the wood structural effect. Such indication of the wood structural effect is quite poor because the plank stiffness measurements can only localize stiffness variations to board areas several feet in length. The additional visual estimates of knot sizes and locations that are required are limited to estimates based on surface observations only. Human observation and interpretation at high speeds introduce further uncertainties. In contrast, density profile measurements allow estimates of the wood structural effect corresponding to localized variations in board areas separated by fractions of an inch. The measurements come from the interior of the wood, and are not limited by what can be seen or interpreted from the surface. No additional human observation of knot sizes or locations is necessary. An additional feature of this invention is its ability to make measurements along the entire length of the wood without directly touching the material.

DESCRIPTION OF THE PREFERRED EMBODIMENTS

Figure 1:
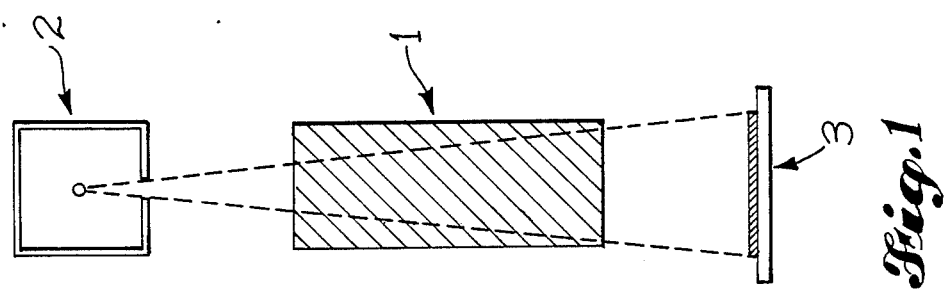
FIG. 1 is a cross-sectional view of a single-detector wood radiation measurement device which operates by measuring the density absorption within the wood.

FIG. 1 shows a cross-section of a piece of lumber 1 situated between a radiation source 2 and a radiation detector 3. The radiation source can be of any suitable type, for example small amounts of Americium 241 or Cesium 137. Likewise, the detector can be of any suitable type, for example an ionization chamber or a scintillation counter. Radiation from the source penetrates the wood, some being absorbed in the wood, and some passing through. The amount of the radiation which passes through the wood is measured by the detector.

For nuclear radiation, the radiation intensity which is measured by the detector depends on the source strength, the local density of the wood material through which the radiation passes, the length of the radiation path within the wood, and a material-dependent constant. Mathematically, this dependence can be expressed by the following formula $$I/I_o = e^{-\rho\mu h}$$

where $\rho =$ local wood density, g/cm$^3$
$\mu =$ attenuation coefficient, $\simeq$ 0.19 cm$^2$/g for Americium 241
$\simeq$ 0.09 cm$^2$/g for Cesium 137

-continued

| | |
|---|---|
| $e =$ | base of natural logarithms |
| $h =$ | wood thickness, cm |
| $I =$ | radiation intensity passing through the wood, counts/cm$^2$/s |
| $I_o =$ | radiation intensity with no wood present, counts/cm$^2$/s |

Solving for density, the formula becomes $$\rho = -\ln(I/I_o)/\mu h$$

If desired, this latter formula can be replaced by approximately equivalent relationships. Most commonly, density measurement will be done at a stage in the wood breakdown process where the wood thickness is constant. This thickness value can then be set as a constant in the above or equivalent formulas. If the local thickness of the wood is not known in advance, the wood thickness may have to be measured by some suitable means. Strength and stiffness estimation procedures will then have to accommodate the variation in overall wood geometry.

A typical diameter of the beam of radiation passing through the wood is about one inch. If radiation intensity measurements are taken at approximately one inch intervals along the length of a piece of wood, then a longitudinal density profile, such as is shown by the solid line in FIG. 2, can be determined. Clearly, the beam width and shape, the increment between density measurements, and the ratio between these two dimensions can be varied over large ranges while remaining within the scope of this invention.

Figure 2:
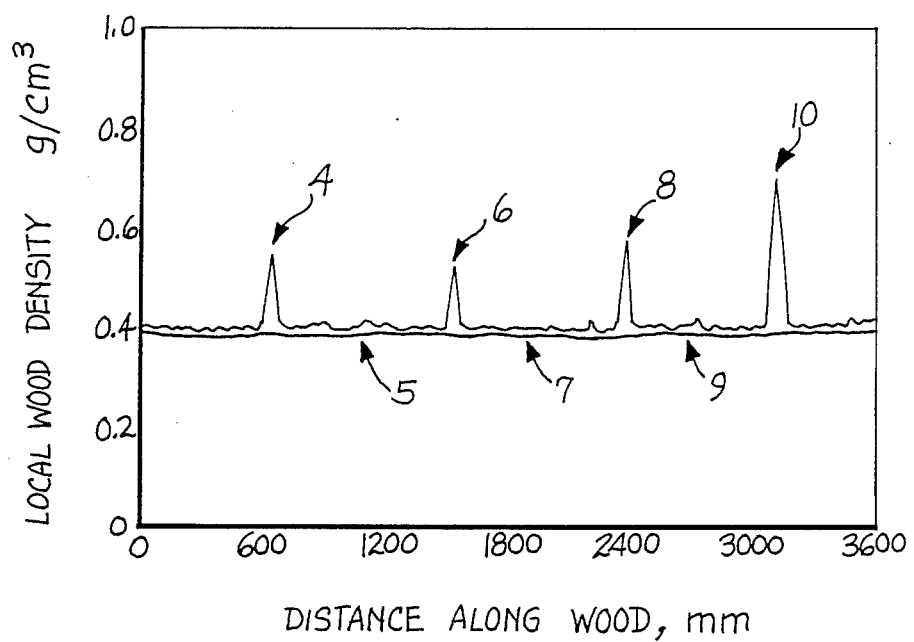
FIG. 2 shows a typical density profile measured along the length of a piece of wood using a device of the type shown in FIG. 1.

In FIG. 2, the sharp peaks in the density profile such as 4, 6, 8 and 10 correspond to knots, and the flat "valley" areas such as 5, 7 and 9 correspond to the clear wood between the knots. The density in the valley areas indicates the inherent (clear) wood strength, and the sizes of the peaks indicate the structural strength reducing effect of the associated knots. The inherent wood strength can be characterized in any way that mainly describes the measured density in the clear wood "valley" areas. Local or overall averages or minima of this clear wood density are among the possibilities. Similarly, the structural effect can be characterized in any way that mainly describes the size of the measured density peaks. The largest height, width, or area of a peak, or any combination of such size measurements are among the possibilities. Also possible are peak size measurements which take into consideration more than one density peak.

The dashed line in FIG. 2 shows the computed clear wood density throughout the wood, ignoring the presence of knots. For clarity, the dashed line has been moved down slightly. This clear wood density profile is useful when identifying the clear wood properties, and when considering the sizes of the knot peaks. The line is computed simply by interpolating between several locally minimum density values along the length of the wood.

Figure 3:
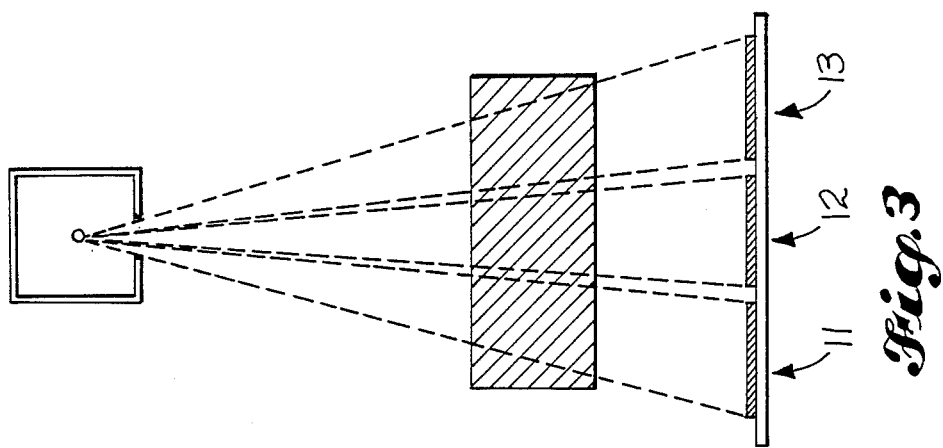
FIG. 3 is a cross-sectional view of a wood density measurement device, similar in principle to that in FIG. 1, with three radiation detectors.

FIG. 3 shows another possible radiation source and detector arrangment. In this particular example, the radiation passes through the wide faces of the wood. There are three radiation detectors 11, 12, and 13 arranged across the width of the wood so as to detect the local density at points close to the two edges of the wood and at the center of the wood. In the same ways as in the single-detector arrangement in FIG. 1, density measurements are repeated at increments along the wood length to form a set of three longitudinal local density profiles. At each wood cross-section, each set of three measurements across the width of the wood constitutes a transverse local density profile. Clearly, the number of radiation detectors across the width of the wood can be other than three and still achieve a similar objective. An advantage of using multiple radiation detectors across the wood width is that they allow the lateral location of a knot to be determined. This is especially important in the case of wood bending strength estimation because in this case edge knots are more significant than center knots. The same is true to a lesser extent for tensile strength estimation. However, even the single detector arrangement in FIG. 1 can give satisfactory tensile strength estimates and modestly accurate estimates of bending strength.

It is clear that many different geometrical configurations of single or multiple radiation sources and detectors could be chosen that could achieve density profile measurement objectives functionally equivalent to those described here. Also, systems could be configured which could provide the grade of the material that may later be cut from the present material. All these configurations fall within the scope of this invention.

Computation of wood strength estimates from multiple density profile data follows a similar concept to that used with single profile data. The clear wood strength comes from a combination of clear wood density measurements from the multiple detectors. The structure effect comes from a combined calculation of the density peaks at and around a knot or knot combination. Typically, the density peaks that are closer to the edge of the wood will be weighted more heavily in this calculation.

In general principle, the wood strength is estimated by starting with a base strength value, then multiplying by a function of clear wood density (to describe the material strength), and further multiplying by a function of density peak size (to describe the structure effect). It is apparent that the clear wood density data and the density peak size data can be combined in many different ways so as to achieve substantially equivalent results. All these calculation methods fall within the scope of this invention.

A specific example of a mathematical formula of the type described above is:

$$\text{estimated strength} = \text{minimum}[B \times \rho o \times 1/(1 + C\Sigma wH)]$$

where
B = base strength of wood, psi
C = calibration constant, $cm^3/g$
$\rho o$ = mean clear wood density, $g/cm^3$
H = height of a density peak, $g/cm^3$
w = weighting factor
$\Sigma$ = summation of the data across the wood width and where "minimum" refers to the minimum value of the right hand side of the equation chosen from among all the transverse density data sets that contain localized density increases. The two material-dependent constants B and C depend on wood species. For example, for Southern Yellow Pine lumber, typical values of B and C are 10000 psi and 6 $cm^3/g$ respectively.

Analogous procedures can be followed to analyze wood density profile data so as to estimate wood stiffness. Typically, such estimates will be inferior in statistical accuracy to wood strength estimates. However, they can be sufficient for many applications. For stiffness estimates, the inherent (clear) wood stiffness, as measured by the clear wood "valley" density is the dominant factor. The structural effect, as measured by the localized density peaks, is less significant.

I claim:

1. A method for estimating the strength or stiffness of a piece of wood comprising:
   measuring the longitudinal density profile of the piece of wood by detecting density at a plurality of longitudinally spaced local areas in the wood,
   identifying and quantifying the features in the wood density profile indicative of the inherent wood strength and the wood structural effects spaced along the length of the wood, and
   using the information derived from the measured wood density profile to estimate the wood strength or stiffness.

2. The method of claim 1 in which the inherent wood strength is identified by portions of the density profile that are relatively constant while the wood structural effects are identified by portions of the density profile that have relatively sharp increases in density caused by the presence of knots.

3. The method of claim 1 wherein the method is used to estimate wood tensile strength.

4. The method of claim 1 wherein the method is used to estimate wood bending strength.

5. The method of claim 1 wherein the method is used to estimate wood tensile stiffness.

6. The method of claim 1 wherein the method is used to estimate wood bending stiffness.

7. The method of claim 1 in which one or more radiation sources and one or more radiation detectors are used for the local wood density measurements.

8. The method of claim 7 where the radiation type is nuclear radiation.

9. The method of claim 7 where the radiation type is microwave radiation.

10. The method of claim 1 in which the local wood density is measured at one or more local areas across the width of the wood.

11. The method of claim 1 in which the local wood density is measured using radiation which is incident to one or more faces of the wood.

* * * * *